(12) United States Patent
Otrembiak et al.

(10) Patent No.: US 10,492,885 B2
(45) Date of Patent: Dec. 3, 2019

(54) ULTRASONIC SURGICAL INSTRUMENT WITH CLEANING PORT

(71) Applicant: Ethicon Endo-Surgery, LLC, Guaynabo, PR (US)

(72) Inventors: Candice Otrembiak, Loveland, OH (US); Charles J. Scheib, Loveland, OH (US); Benjamin M. Boyd, Fariborn, OH (US); Amelia A. Pierce, Cincinnati, OH (US); Rafael J Ruiz Ortiz, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 605 days.

(21) Appl. No.: 14/972,995

(22) Filed: Dec. 17, 2015

(65) Prior Publication Data

US 2017/0172699 A1    Jun. 22, 2017

(51) Int. Cl.
    *A61B 17/32*     (2006.01)
    *A61B 18/00*     (2006.01)
    (Continued)

(52) U.S. Cl.
CPC ...... *A61B 90/70* (2016.02); *A61B 17/320068* (2013.01); *A61B 17/320092* (2013.01); *A61B 18/1445* (2013.01); *A61B 2017/320084* (2013.01); *A61B 2017/320094* (2017.08); *A61B 2017/320095* (2017.08);
(Continued)

(58) Field of Classification Search
CPC ............. A61B 90/70; A61B 2090/701; A61B 2017/320084; A61B 17/320068; A61B 2017/32007; A61B 2017/320071; A61B 2017/320072; A61B 2017/320073; A61B 2017/320074; A61B 2017/320075; A61B 2017/320077; A61B 2017/32113; A61B 17/22012; A61B 2017/22014; A61B 2017/22015; A61F 9/00709; A61F 9/00736; A61F 2/962; A61F 2/966; A61F 2/848; A61F 2002/8483; A61F 2002/8486; A61F 2/013; A61F 2002/011
See application file for complete search history.

(56) References Cited

U.S. PATENT DOCUMENTS 5,322,055 A    6/1994   Davison et al.
5,324,299 A    6/1994   Davison et al.
(Continued)

OTHER PUBLICATIONS

Merriam-Webster definition for "colocate" as accessed Dec. 19, 2018; https://www.merriam-webster.com/dictionary/colocate.*
(Continued)

*Primary Examiner* — Wade Miles
(74) *Attorney, Agent, or Firm* — Frost Brown Todd LLC

(57) ABSTRACT

A surgical instrument includes a shaft assembly and an end effector. The shaft assembly includes a shaft having a proximal end and a distal end. A lumen extends along at least a portion of the shaft. A lateral opening is formed in the shaft at a longitudinal position between the proximal and distal ends. The lateral opening is in fluid communication with the lumen. The shaft assembly further includes a movable member that is configured to selectively cover the opening. The end effector is at the distal end of the shaft. The lumen and the lateral opening may be used to flush debris and bodily fluids from the lumen and other regions of the shaft assembly.

20 Claims, 9 Drawing Sheets

(51) Int. Cl.
*A61B 18/14* (2006.01)
*A61B 90/70* (2016.01)
(52) U.S. Cl.
CPC ............... *A61B 2018/0063* (2013.01); *A61B 2018/00595* (2013.01); *A61B 2018/00619* (2013.01)

(56) References Cited

U.S. PATENT DOCUMENTS

| | | | |
|---|---|---|---|
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,520,983 B1* | 2/2003 | Colgan | A61F 2/90 623/1.11 |
| 6,773,444 B2 | 8/2004 | Messerly | |
| 6,783,524 B2 | 8/2004 | Anderson et al. | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,149,291 B2 | 10/2015 | Parham et al. | |
| 9,271,751 B2 | 3/2016 | Houser et al. | |
| 2001/0051784 A1* | 12/2001 | Brisken | A61B 17/22012 604/22 |
| 2002/0002401 A1* | 1/2002 | McGuckin, Jr. | A61B 17/12109 623/1.19 |
| 2002/0029054 A1* | 3/2002 | Rabiner | A61B 17/320068 606/169 |
| 2006/0079874 A1 | 4/2006 | Faller et al. | |
| 2006/0161189 A1* | 7/2006 | Harp | A61B 17/1624 606/171 |
| 2006/0200191 A1* | 9/2006 | Zadno-Azizi | A61B 17/12045 606/200 |
| 2007/0011713 A1 | 1/2007 | Abramson et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2008/0234709 A1* | 9/2008 | Houser | A61B 17/320068 606/169 |
| 2008/0234710 A1* | 9/2008 | Neurohr | A61B 17/320068 606/169 |
| 2009/0036914 A1* | 2/2009 | Houser | A61B 17/29 606/169 |
| 2009/0105653 A1* | 4/2009 | Spenser | A61F 2/013 604/164.13 |
| 2011/0137335 A1* | 6/2011 | Hallisey | A61F 2/01 606/200 |
| 2012/0112687 A1 | 5/2012 | Houser et al. | |
| 2012/0116265 A1 | 5/2012 | Houser et al. | |
| 2014/0005701 A1 | 1/2014 | Olson et al. | |
| 2015/0080924 A1 | 3/2015 | Stulen et al. | |
| 2015/0245850 A1 | 9/2015 | Hibner et al. | |
| 2015/0273244 A1 | 10/2015 | Akagane | |

OTHER PUBLICATIONS

Merriam-Webster definition for "coextensive" as accessed Dec. 19, 2018; https://www.merriam-webster.com/dictionary/coextensive.*
U.S. Appl. No. 61/410,603, filed Nov. 5, 2010.
International Search Report and Written Opinion dated Jun. 13, 2017 for Application No. PCT/US2016/066455, 14 pgs.

* cited by examiner

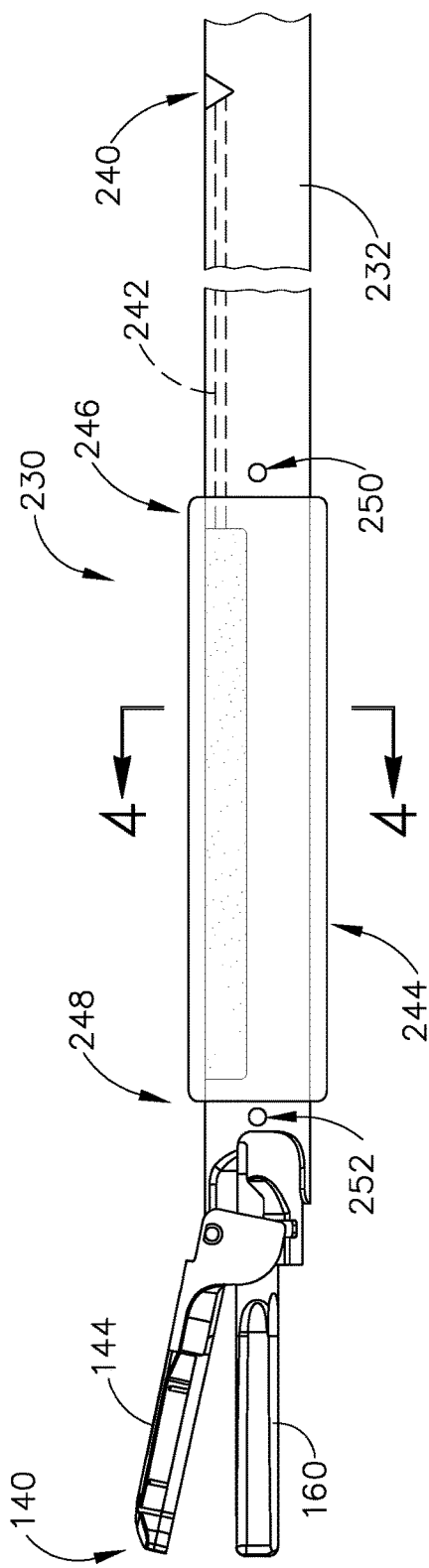
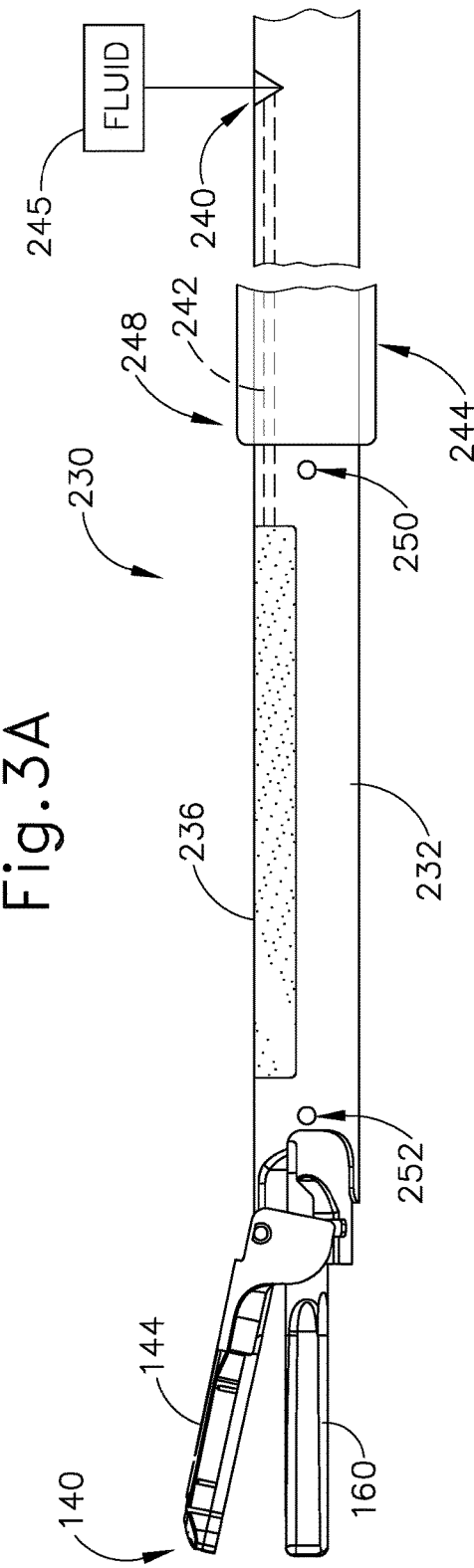

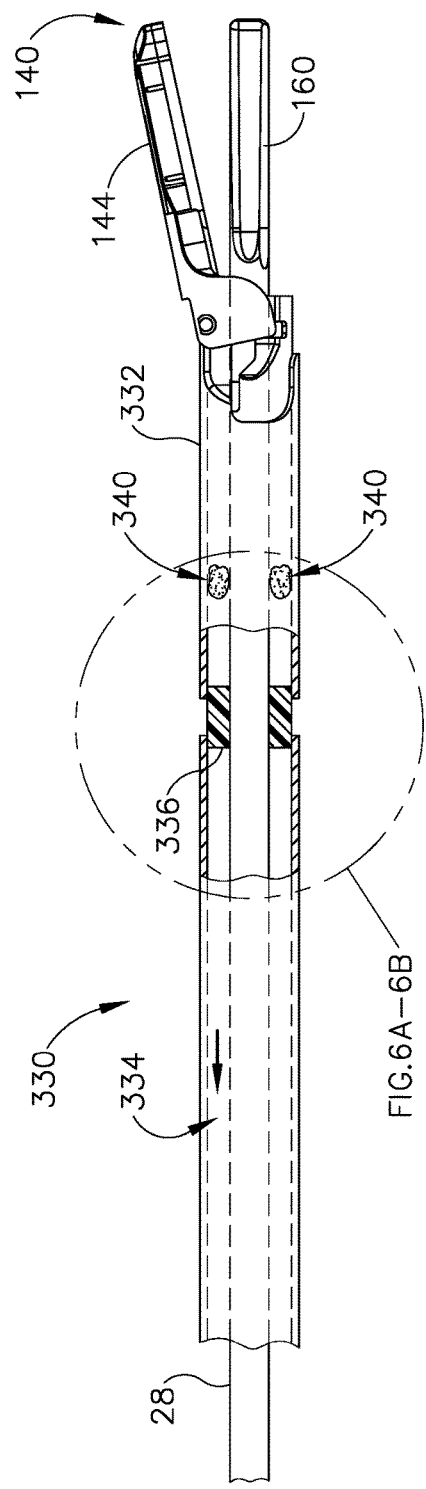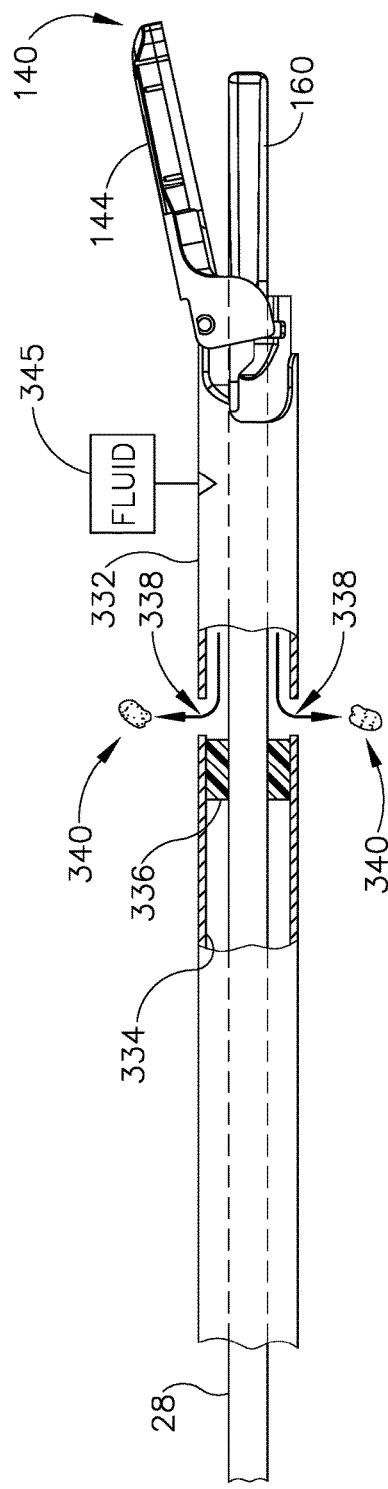
Fig. 5A
Fig. 5B

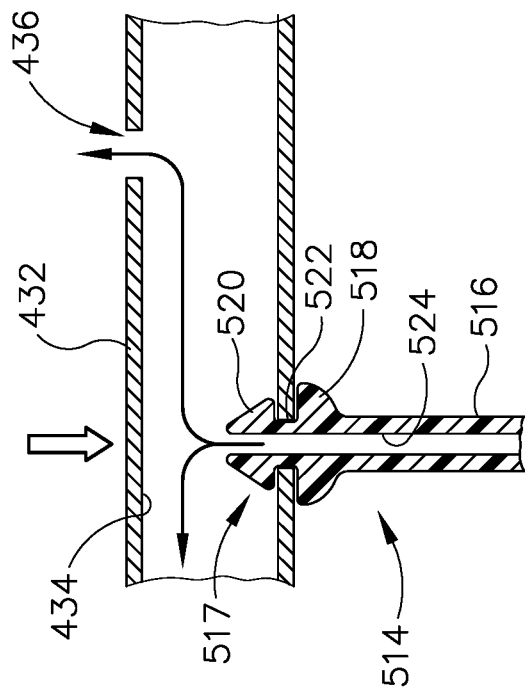
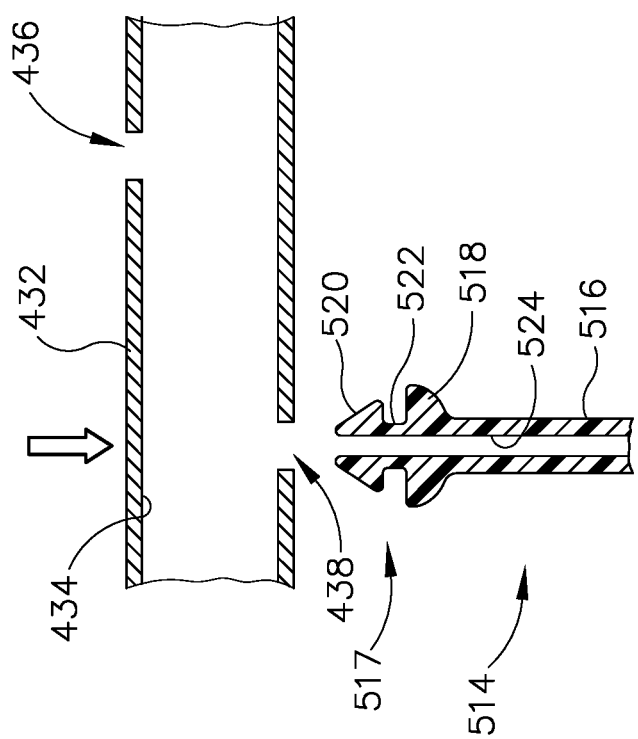
Fig.8A
Fig.8B

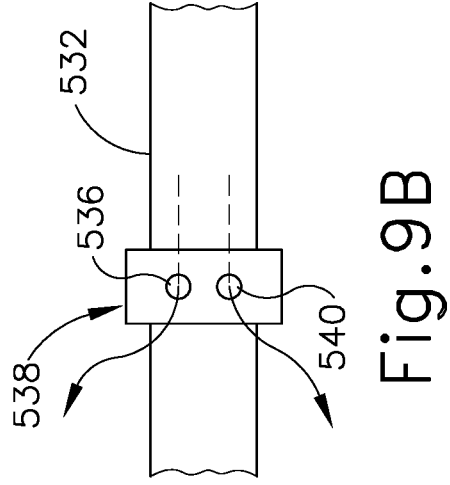
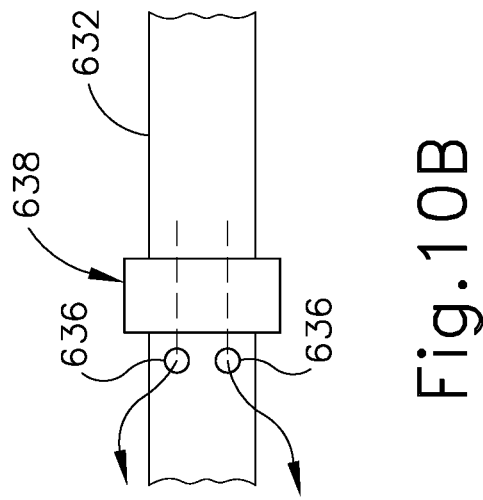
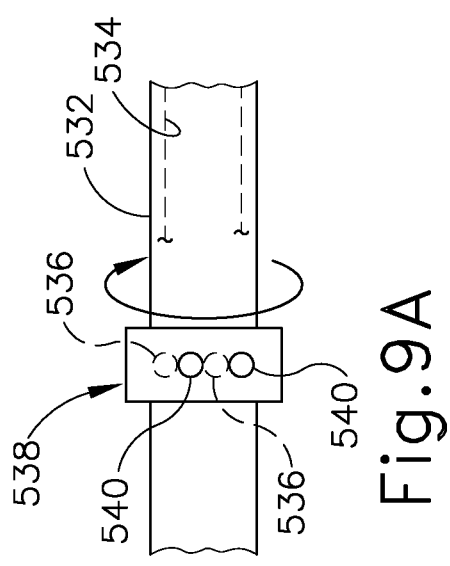
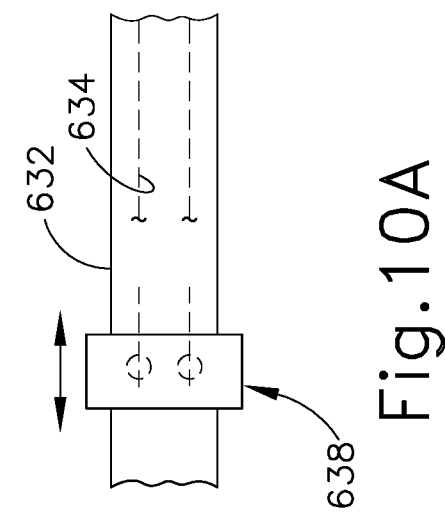

ULTRASONIC SURGICAL INSTRUMENT WITH CLEANING PORT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevational view of an exemplary alternative shaft assembly that is suitable for incorporation into the surgical instrument of FIG. 2, showing a slidable shaft portion in a distal position;

FIG. 3B depicts a side elevational view of the shaft assembly of FIG. 3A, showing the slidable shaft portion in a proximal position to expose a cleaning feature;

FIG. 5A a side elevational view of another exemplary alternative shaft assembly that is suitable for incorporation into the surgical instrument of FIG. 2, showing a cleaning port of the shaft assembly in a closed state;

FIG. 5B depicts a side elevational view of the shaft assembly of FIG. 5A, showing the cleaning port of the shaft assembly in an open state;

FIG. 8A depicts a cross-sectional side view of a connection port of the cleaning tray of FIG. 7 and a portion of the shaft assembly of FIG. 7, prior to the connection port and the shaft assembly being coupled to one another;

FIG. 8B depicts a cross-sectional side view of the connection port and the portion of the shaft assembly shown in FIG. 8A, showing the connection port and the shaft assembly coupled to one another;

FIG. 9A depicts a plan view of an exemplary outlet port of the cleaning tray of FIG. 7, showing a movable member in a first position preventing fluid from flowing out of outlets of the outlet port;

FIG. 9B depicts a plan view of the outlet port of FIG. 9A, showing the movable member in a second position to allow fluid to flow out of the outlets;

FIG. 10A depicts a plan view of an exemplary alternative outlet port of the cleaning tray of FIG. 7, showing an exemplary alternative movable member in a first position preventing fluid from flowing out of outlets of the outlet port; and FIG. 10B depicts a plan view of the outlet port of FIG. 10A, showing the movable member in a second position to allow fluid to flow out of the outlets.

Figure 1:
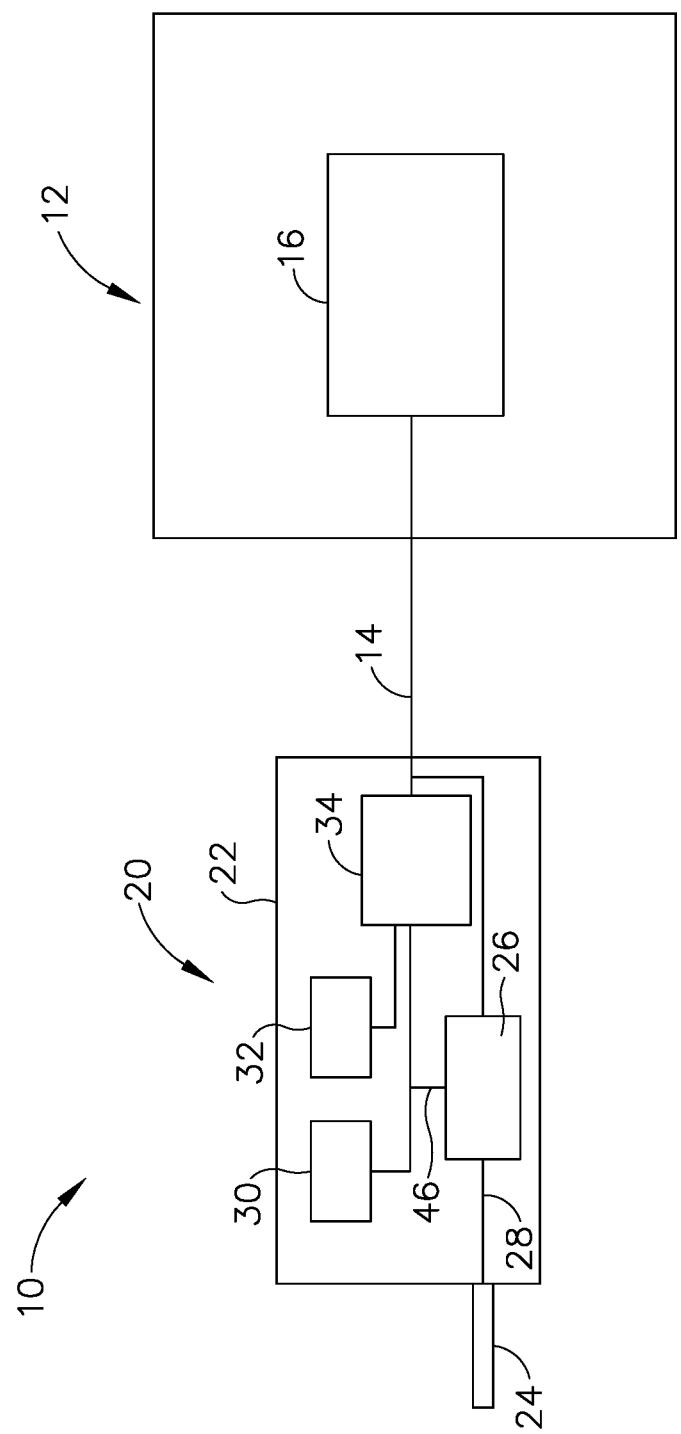
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nX/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
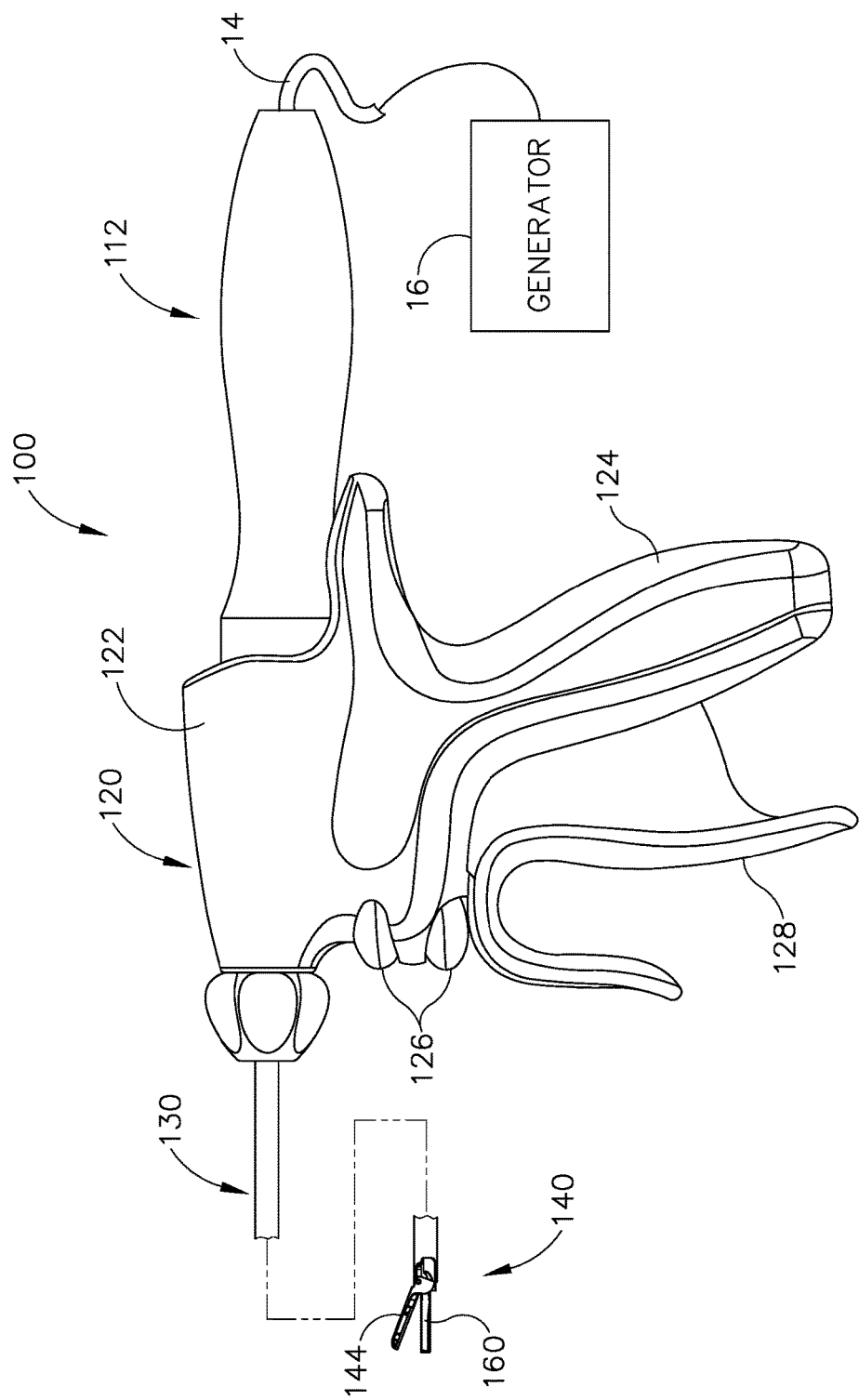
FIG. 2 depicts a side elevational view of an exemplary form that the instrument of FIG. 1 may take.

FIG. 2 illustrates an exemplary ultrasonic surgical instrument (110). At least part of instrument (110) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on Mar. 5, 2015; U.S. Pub. No. 2012/0112687, issued as U.S. Pat. No. 9,371,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (110) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (110), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube and an outer tube that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the communication of ultrasonic vibration from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (136) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (144) and blade (160). In particular, activation of a second one of the buttons (136) may cause vibration of ultrasonic blade (160) at a relatively high amplitude. Other suitable operational modes that may be associated with buttons (126) will be apparent to persons skilled in the art in view of the teachings herein.

III. Exemplary Alternative Shaft Assemblies

While instruments such as instrument (110) are effective for cutting and sealing tissue as described above, using energy to treat tissue may result in debris becoming stuck to end effector (40, 140) and other portions of instrument (110). For example, debris may be forced into portions of shaft assembly (130), particularly in a gap or lumen formed between the outer surface of waveguide (28) and the inner surface of the inner tube of shaft assembly (130). It will be appreciated that the design and structure of such instruments (110) may make it difficult to clean the internal portions of instrument (110) components, such as shaft assembly (130). It may therefore be desirable to include features in shaft assembly (130) or other portions of instrument (110) that enable instrument (110) to be more easily cleaned before sterilization and reuse. Various examples of features that may be used to facilitate cleaning of shaft assembly (130) are described in greater detail below.

A. Shaft Assembly Including Sleeve Selectively Covering Elongate Cleaning Opening FIGS. 3A-4B show an exemplary alternative shaft assembly (230) that is suitable for incorporation into a surgical instrument, such as surgical instrument (10, 110). It should therefore be understood that shaft assembly (230) may be used in place of shaft assembly (130). Shaft assembly (230) of this example includes end effector (140), which is configured and operable substantially identically to end effector (140) described above. The details of end effector (140) will therefore not be repeated here. It should be understood, however, that shaft assembly (230) of this example is not limited to use with end effector (140). By way of example only, shaft assembly (230) may instead be readily combined with end effectors that are operable to apply electrosurgical energy to tissue, end effectors that are operable to apply staples to tissue, end effectors that are operable to apply sutures to tissue, end effectors that are operable to apply clips to tissue, etc. Various other suitable kinds of end effectors that may be combined with shaft assembly (230) will be apparent to those of ordinary skill in the art in view of the teachings herein.

Figure 4A:
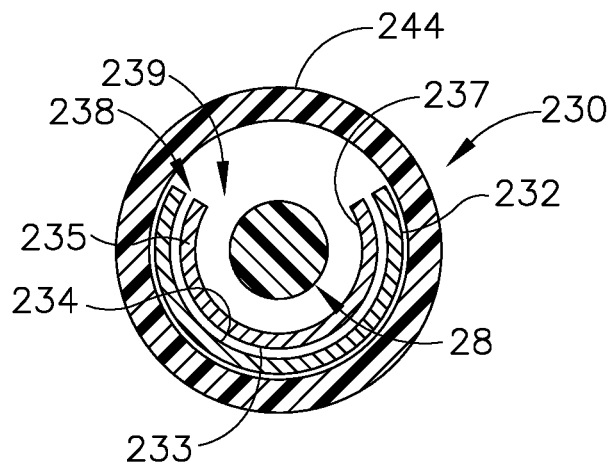
FIG. 4A depicts a cross-sectional view of the shaft assembly of FIG. 3A, taken along line 4-4 of FIG. 3A, showing the slidable shaft portion in the distal position of FIG. 3 A.
Figure 4B:
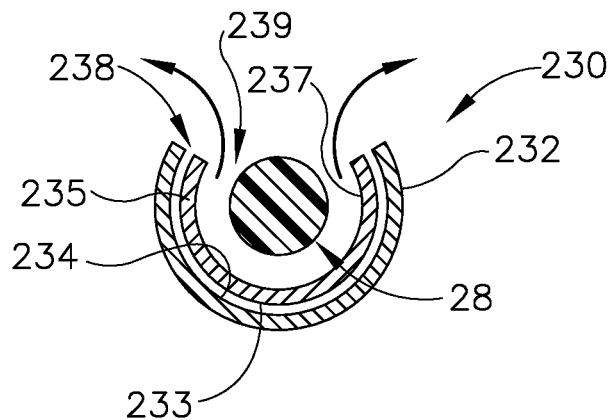
FIG. 4B depicts a cross-sectional view of the shaft assembly of FIG. 3A, taken along line 4-4 of FIG. 3A, showing the slidable shaft portion in the proximal position of FIG. 3B.

As best seen in FIGS. 4A-4B, shaft assembly (230) of the present example comprises an outer tube (232) and an inner tube (233). Outer tube (232) has an inner surface (234) and defines an elongate lateral opening (238). Inner tube (233) is coaxially disposed in outer tube (232). Inner tube (233) has outer and inner surfaces (235, 237) and defines an elongate lateral opening (239). Lateral openings (238, 239) are longitudinally co-located and coextensive with each other when clamp arm (144) is in the open position. Waveguide (28) is coaxially disposed in inner tube (233). A gap or lumen is defined between surfaces (234, 235) of tubes (232, 233). Both tubes (232, 233) are pivotably coupled with clamp arm (144) as noted above, such that relative longitudinal movement between tubes (232, 233) will provide pivotal movement of clamp arm (144) toward and away from blade (160).

As shown in FIGS. 3A-3B, outer tube (232) further defines a fluid port (240) that is in fluid communication with the gap defined between surfaces (234, 235) of tubes (232, 233). Fluid port (240) is located at the proximal end of shaft assembly (230); while openings (238, 239) are located at the distal end of shaft assembly (230). As shown, fluid port (240) may be coupled with a fluid source (245), which may include any suitable fluid (e.g., saline, etc.). In the present example, fluid from fluid source (245) may be driven through port (240) to flush debris and/or bodily fluids from the gap defined between surfaces (234, 235) of tubes (232, 233). Once the fluid reaches openings (238, 239), the fluid may further flush any debris and/or bodily fluids from the gap defined between waveguide (28) and inner tube (233). The fluid, flushed debris, and flushed bodily fluids may ultimately escape from shaft assembly (230) via openings (238, 239).

Shaft assembly (230) further includes an elongate sleeve (244) that is configured to selectively cover opening (238). In particular, sleeve (244) is configured to translate between a distal position (FIGS. 3A and 4A) and a proximal position (FIGS. 3B and 4B). Sleeve (244) has a proximal end (246) and a distal end (248). The length between ends (246, 248) is longer than the length of opening (238), such that sleeve (244) may cover the entire length of opening (238) when sleeve (244) is in the distal position. In some examples, sleeve (244) may include annular sealing members at the proximal and distal ends (246, 248) such that when sleeve (244) is positioned to cover opening (238) (in the distal position shown in FIG. 3A), sleeve (244) effectively seals opening (238) such that substantially no fluids may enter or exit from opening (238). When sleeve (244) is in the proximal position, opening (238) is uncovered. It should be understood that sleeve (244) does not cover or otherwise interfere with port (240) when sleeve (244) is in the proximal position.

In the present example, sleeve (244) is maintained in the first position by a proximal pin (250) and a distal pin (252). Distal pin (250) prevents the distal advancement of sleeve (244) past a certain distal position, while proximal pin (252) prevents the proximal movement of sleeve (244). Thus, distal and proximal pins (250, 252) substantially prevent axial movement of sleeve (244). In the example shown, proximal pin (252) is resiliently biased away from the longitudinal axis of shaft assembly (230) (e.g., like a pogo pin). In order to allow proximal movement of sleeve (244), pin (252) may be directed or pushed inwardly toward the longitudinal axis of shaft assembly (230) such that proximal pin (252) no longer impedes or otherwise prevents the proximal movement of sleeve (244). Sleeve (244) may thereby be moved to the proximal position as shown in FIG. 3B. Moreover, in the example shown, once the distal end (248) is positioned proximally of pin (252), proximal pin (252) may extend back outwardly. Proximal pin (252) may thus substantially prevent distal movement of sleeve (244) when sleeve (244) is in the proximal position. Distal pin (250) may also be resiliently biased outwardly yet deflectable inwardly, permitting sleeve (244) to be completely removed from shaft assembly (230) if desired.

While only one distal pin (250) and one proximal pin (252) are shown, some versions may include multiple distal pins (250) and/or multiple proximal pins (252). For example, there may be two opposing distal pins (250) or more than two distal pins (250). Similarly, there may be two opposing proximal pins (252) or more than two opposing proximal pins (252). In addition or in the alternative, shaft assembly (230) may include other elements or mechanisms that are configured to maintain the position of sleeve (244), such as a detent mechanism(s), resilient member(s), etc. In addition to or as an alternative to pins (250, 252), in versions where sleeve (244) has inner elastomeric sealing members bearing against the outer surface of outer tube (232), the engagement of these sealing members may provide sufficient friction to substantially maintain the longitudinal position of sleeve (244) along outer tube (232); while still permitting intentional movement of sleeve (244) along outer tube (232). Other suitable features that may be used to limit or prevent the movement of sleeve (244) relative to outer tube (232) will be apparent to persons skilled in the art in view of the teachings herein.

As noted above, fluid from fluid source (245) may be driven through port (240) to flush debris and/or bodily fluids from interior regions of shaft assembly (230). This may allow flushing to be performed while sleeve (244) is in the proximal position, such that the fluid, flushed debris, and flushed bodily fluids may ultimately escape from shaft assembly (230) via openings (238, 239). In some instances, it may be desirable to drive fluid from fluid source (245) through port (240) while sleeve (244) is still in the distal position or some position between the distal and proximal positions. This may be done for a certain period of time to build up fluid pressure in the interior regions of shaft assembly (230), before sleeve (244) is retracted proximally to allow fluids and debris to escape via openings (238, 239). It should also be understood that fluid source (245) may be configured to provide fluid at a pressure and flow rate that is sufficient to dislodge debris in shaft assembly (230) without requiring the use of sleeve (244) to provide a pressure buildup. Various suitable fluid pressures and flow rates will be apparent to persons skilled in the art in view of the teachings herein.

B. Shaft Assembly Including Bumper Coincident with Shaft Opening

FIGS. 5A-6B show an exemplary alternative shaft assembly (330) that is suitable for incorporation into a surgical instrument, such as surgical instrument (10, 110). It should therefore be understood that shaft assembly (330) may be used in place of shaft assembly (130). Shaft assembly (330) of this example includes end effector (140), which is configured and operable substantially identically to end effector (140) described above. The details of end effector (140) will therefore not be repeated here. It should be understood, however, that shaft assembly (330) of this example is not limited to use with end effector (140). By way of example only, shaft assembly (330) may instead be readily combined with end effectors that are operable to apply electrosurgical energy to tissue, end effectors that are operable to apply staples to tissue, end effectors that are operable to apply sutures to tissue, end effectors that are operable to apply clips to tissue, etc. Various other suitable kinds of end effectors that may be combined with shaft assembly (330) will be apparent to those of ordinary skill in the art in view of the teachings herein.

Figure 6A:
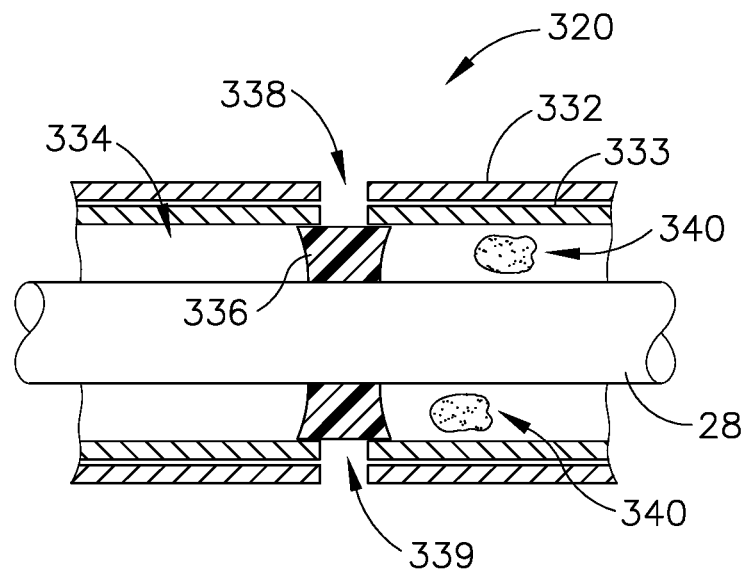
FIG. 6A depicts a detailed view of the shaft assembly of FIG. 5A, showing the cleaning port in the closed state.
Figure 6B:
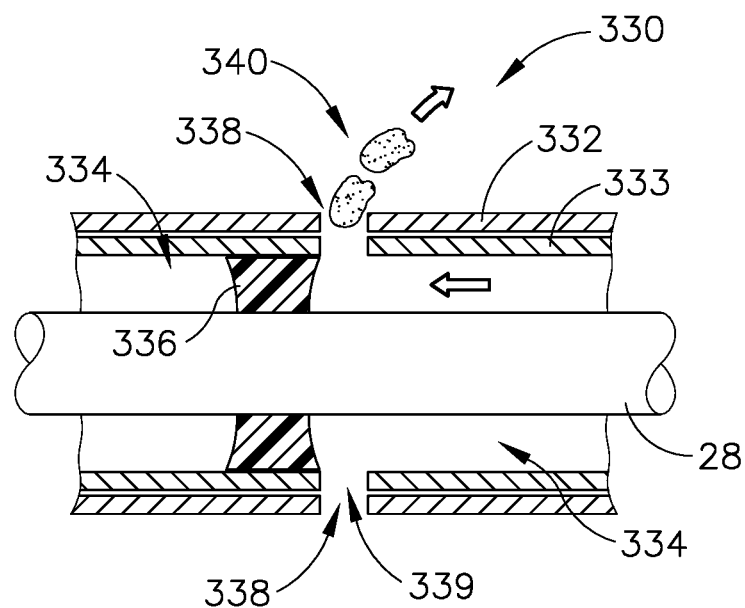
FIG. 6B depicts a detailed view of the shaft assembly of FIG. 5A, showing the cleaning port in the open state.

As best seen in FIGS. 6A-6B, shaft assembly (330) of the present example comprises an outer tube (332) and an inner tube (333). It should be understood that inner tube (333) is omitted from FIGS. 5A-5B for clarity. Outer tube (332) defines a pair of lateral openings (338), which are diametrically opposed to each other. It should be understood that other versions of outer tube (332) may include more or fewer than two lateral openings (338). Inner tube (333) is coaxially disposed in outer tube (332). Inner tube (333) also defines a pair of lateral openings (339), which are diametrically opposed to each other. It should be understood that other versions of inner tube (333) may include more or fewer than two lateral openings (339). Lateral openings (338, 339) are longitudinally co-located and coextensive with each other when clamp arm (144) is in the open position. Waveguide (28) is coaxially disposed in inner tube (333). A lumen or gap (334) is defined between the interior of inner tube (333) and the exterior of waveguide (288). Both tubes (332, 333) are pivotably coupled with clamp arm (144) as noted above, such that relative longitudinal movement between tubes (332, 333) will provide pivotal movement of clamp arm (144) toward and away from blade (160).

Shaft assembly (330) also includes a bumper (336) positioned coaxially around waveguide (28) and within inner tube (333). As shown, bumper (336) assists in maintaining the radial position of waveguide (28) within shaft assembly (330), and attenuates vibrations from waveguide (28) to other components of shaft assembly (330). Bumper (336) is located at a longitudinal position along waveguide (28) corresponding to a node associated with ultrasonic vibrations communicated through waveguide (28). In the present example, bumper (336) comprises an annular member that is sized to provide an interference fit within inner tube (333). However, bumper (336) is slidable within inner tube (333) and may include a lubricious coating to allow for such relative movement. Bumper (336) of the present example comprises an elastomeric material but in other examples may comprise any suitable material. Bumper (336) provides as a fluid barrier between the distal portion of gap (334) and the remaining portions of gap (334) that are proximal to bumper (336), such that bumper (336) essentially seals the proximal portion of gap (334) from a more distal portion of gap (334).

Shaft assembly (330) is configured such that relative longitudinal movement is possible between waveguide (28) and the combination of tubes (332, 333). In some versions, waveguide (28) is configured to translate longitudinally while tubes (332, 333) remain stationary. By way of example only, shaft assembly (330) may provide longitudinal movement of waveguide (28) and blade (160) relative to tubes (332, 333) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In some other versions, tubes (332, 333) are configured to translate together longitudinally while waveguide (28) remains stationary. Various suitable ways in which such relationships may be provided will be apparent to those of ordinary skill in the art in view of the teachings herein.

FIGS. 5A and 6A show waveguide (28) and tubes (332, 333) in a relative positioning that would be provided during use of shaft assembly (330) and end effector (140) during a surgical procedure. The longitudinal position of blade (160) is substantially the same as the longitudinal position of clamp arm (144). In this state, bumper (336) is coincident with openings (338, 339) such that bumper (336) covers openings (338, 339). Bumper (336) thus blocks fluid communication through openings (338, 339).

FIGS. 5B and 6B show waveguide (28) and tubes (332, 333) in a relative positioning that would be provided in order to clean interior regions of shaft assembly (330). The longitudinal position of blade (160) is proximal in relation to the longitudinal position of clamp arm (144). In this state, bumper (336) is located proximally in relation to openings (338, 339), such that bumper (336) no longer blocks fluid communication through openings (338, 339). Thus, fluid may be directed into gap (334) from a fluid source (345) in order to clean gap (334) and clear debris (340) and bodily fluids from gap (334). The flushed debris (340) and fluids will exit openings (338, 339). In some versions, fluid may be directed into gap (334) when bumper (336) is still in a position covering openings (338, 339), so as to build up fluid pressure in gap (334) before shaft assembly (330) is transitioned to the state shown in FIGS. 5B and 6B. It should also be understood that fluid source (345) may be configured to provide fluid at a pressure and flow rate that is sufficient to dislodge debris in shaft assembly (330) without requiring the use of bumper (336) to provide a pressure buildup. Various suitable fluid pressures and flow rates will be apparent to persons skilled in the art in view of the teachings herein.

IV. Exemplary Cleaning System

As described above, shaft assemblies (230, 330) may receive fluids to flush debris and bodily fluids from interior regions of shaft assembly (230, 330). Those of ordinary skill in the art will recognize that this process may tend to be rather messy. It may therefore be desirable to provide a fixture and/or environment where such flushing procedures may be performed in a way that captures the flushed fluids and debris, minimizing contact between the human operators and the fluid fluids/debris. Merely illustrative examples of a cleaning system that provide such a contained fixture and environment will be described in greater detail below, while other examples will be apparent to those of ordinary skill in the art in view of the teachings herein.

A. Exemplary Cleaning Tray and Surgical Instrument Including Cleaning Ports

Figure 7:
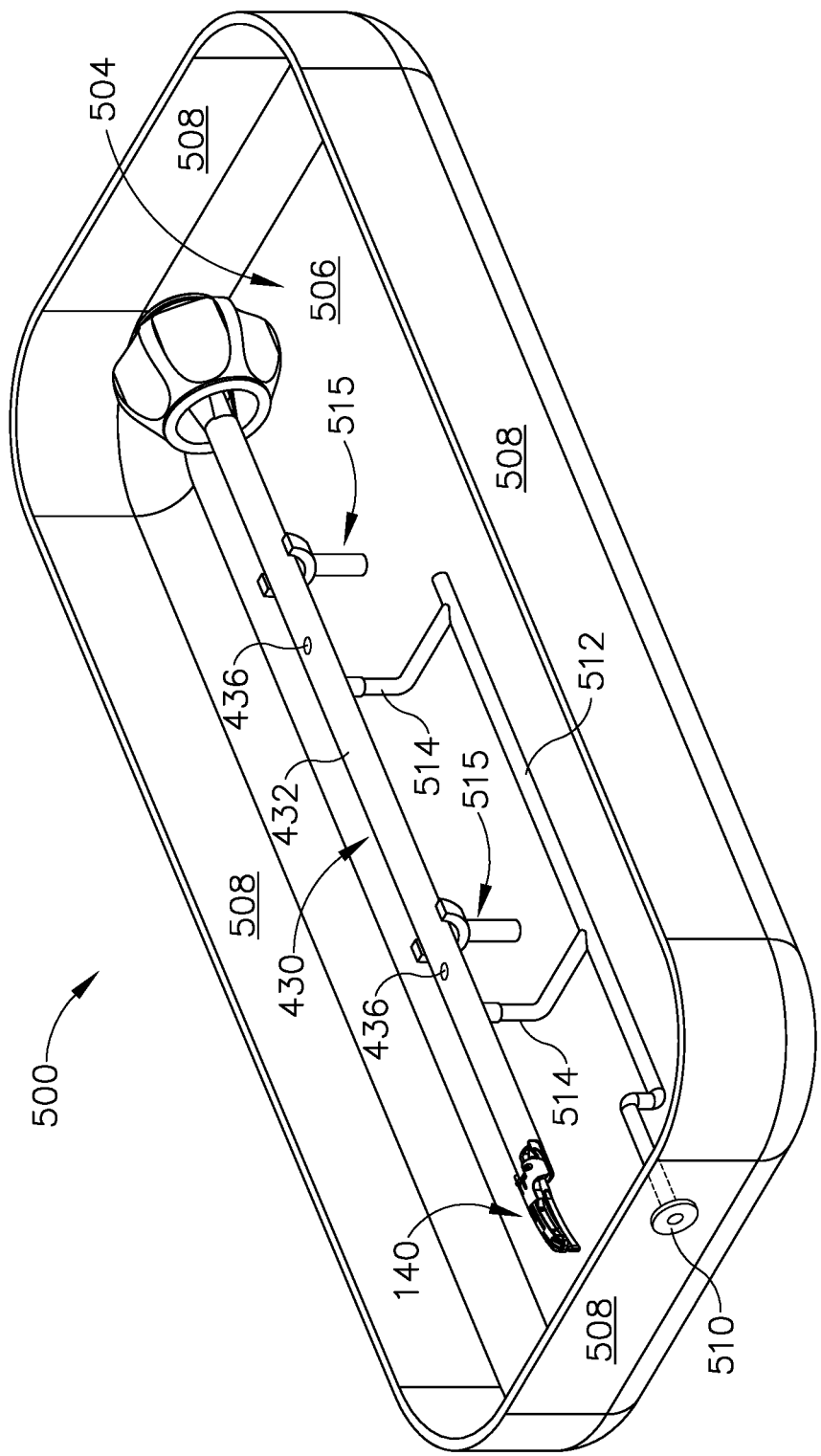
FIG. 7 depicts a perspective view of an exemplary cleaning tray, showing a shaft assembly of a surgical instrument fluidly connected thereto.

FIG. 7 shows an exemplary alternative shaft assembly (430) that is mechanically and fluidly coupled to a cleaning tray (500). Shaft assembly (430) is configured to be removably coupled with handle assembly (120) in the present example. In some versions, handle assembly (120) is configured to separate into two pieces, with shaft assembly (430) being secured to one of the portions of handle assembly (120) and being removable from the other portion of handle assembly (120). By way of example only, such a configuration may be provided in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein.

It should be understood that shaft assembly (430) may be configured and operable just like shaft assembly (130) described above, with the additional features and operability described below. Shaft assembly (430) of this example includes end effector (140), which is configured and operable substantially identically to end effector (140) described above. The details of end effector (140) will therefore not be repeated here. It should be understood, however, that shaft assembly (430) of this example is not limited to use with end effector (140). By way of example only, shaft assembly (430) may instead be readily combined with end effectors that are operable to apply electrosurgical energy to tissue, end effectors that are operable to apply staples to tissue, end effectors that are operable to apply sutures to tissue, end effectors that are operable to apply clips to tissue, etc. Various other suitable kinds of end effectors that may be combined with shaft assembly (430) will be apparent to those of ordinary skill in the art in view of the teachings herein.

Tray (500) of the present example includes a tray body (502) defining a cavity (504). Particularly, cavity (504) is defined by a bottom surface or wall (506) and a plurality of sidewalls (508). Tray (500) includes a tray inlet port (510), a main conduit (512), and two tray outlet ports (514). As discussed in further detail below, outlet ports (514) are configured to fluidly couple to a shaft assembly of a surgical instrument, such as shaft assembly (430). Tray (500) further includes two support members (515) having U-shaped holding portions that are configured to receive and support shaft assembly (430).

In the present example, shaft assembly (430) includes a shaft (432) defining a lumen (434). As shown, shaft (432) including a set of upper lateral openings (436) and set of lower lateral openings (438) that are angularly opposed to and axially offset from upper openings (436). Shaft (432) may include additional openings, such as openings on the sides or other portions of shaft (432). It will be understood that terms such as "upper" and "lower" are terms of reference based on the view(s) shown in the FIGS. and that features such as the opening may be in configurations such that they may not be considered to be "upper" and "lower". It should also be understood that shaft (432) may include inner tubes and outer tubes like the various inner tubes and outer tubes described above. Openings (436, 438) may thus be formed through sidewalls of both the inner tube and the outer tube. It should also be understood that a waveguide such as waveguide (28) may be positioned within shaft (432). In some other versions, however, waveguide (28) remains coupled with handle assembly (120) when shaft assembly (430) is removed from handle assembly (120) in order to engage shaft assembly (430) in tray (500). In still other versions, shaft assembly (430) is capable of engaging tray (500) while handle assembly (120) is still coupled with shaft assembly (430).

As shown in FIGS. 8A-8B, each tray outlet port (514) includes a hollow shaft (516) that extends from main conduit (512), and a connecting feature (517). Connecting feature (517) includes a proximal rib (518), a distal rib (520), and a groove (522) in between proximal and distal ribs (518, 520). Distal rib (518) comprises a tapered end. Shaft (516) defines a conduit (524) extending from a distal end thereof to a proximal end thereof, which fluidly connects with main conduit (512), such that fluid directed into main conduit (512) may also be directed through and out of conduit (524). Thus, fluidly connecting conduits (524) of tray outlet ports (514) with lumen (434) of shaft (432) will enable fluid to flow through main conduit (512), tray outlet ports (514), and into lumen (434).

As shown best in FIGS. 8A-8B, in order to fluidly couple lumen (534) to conduits (524), an operator may direct openings (438) toward connecting features (517) of tray (500). In the example shown tray outlet ports (514) are spaced apart the same distance as the spacing between openings (438). Distal rib (520) enters the opening (438) and sidewall of shaft (432) engages groove. In the example shown, connecting feature (517) essentially seals the openings (438) such that fluid is substantially prevented from exiting the openings (438). Thus, fluid may be directed into main conduit (512) from a fluid source (545). The fluid may then travel into conduits (524), into lumen (334) from fluid source (345) in order to clean lumen (334) and clear debris (340) from lumen (334). As fluid is directed into lumen (334), fluid and debris will also be drawn out from openings (436). Fluid from fluid source may be pressurized at a sufficient pressure such that the flow rate of fluid into lumen is sufficient to dislodge any debris that is present in lumen (334). Such pressures and flow rates will be apparent to persons skilled in the art in view of the teachings herein.

In some versions, the fluid and debris that is flushed from shaft assembly (430) exits the distal end of shaft assembly (430), the proximal end of shaft assembly (430), and/or some other exit port(s) of shaft assembly (430). In such versions, tray (500) may capture such flushed fluid and debris. Tray (500) may also include a drain feature that provides drainage of the flushed fluid and debris. Other suitable ways in which shaft assembly (430) may be fluidly coupled with tray inlet port (510) will be apparent to those of ordinary skill in the art in view of the teachings herein. Similarly, other suitable ways in which fluid and debris that is flushed from shaft assembly (430) may be handled will be apparent to those of ordinary skill in the art in view of the teachings herein.

B. Exemplary Alternative Shafts

FIGS. 9A-9B and 10A-10B show exemplary alternative shafts (532, 632), respectively, that are suitable for incorporation into shaft assembly (430), such as for use in combination with cleaning tray (500). However, shafts (532, 632) are each also suitable for incorporation into shaft assemblies (130, 230, 330) or other suitable shaft assemblies. As shown, shaft (532) includes a lumen (534) and a plurality of lateral openings (536). In the example shown, openings (536) may be used as outlets, similar to openings (436) in shaft (432) above, to allow fluid and debris to escape from lumen (534), though openings (536) are not so limited. In addition or in the alternative, openings (536) may be used as inlets to allow a flushing fluid to enter lumen (534). Shaft (532) includes a movable member (538) having a set of openings (540) that correspond to the size and angular position of openings (536) in shaft (532). As shown in FIG. 9A, in a first rotational position, openings (540) are not aligned with openings (536), such that movable member (538) blocks fluid from escaping from openings (536) and thus also lumen (534). However, movable member (536) is rotatable to a position shown in FIG. 9B where openings (540) are aligned with openings (536), and thus fluid may escape from lumen (534) out of openings (536).

Referring to FIGS. 10A-10B, shaft (632) includes a lumen (634) and a plurality of openings (636). In the example shown, openings (636) may be used as outlets, similar to openings (436) in shaft (432) above, to allow fluid and debris to escape from lumen, though openings (636) are not so limited. In addition or in the alternative, openings (636) may be used as inlets to allow a flushing fluid to enter lumen (634). As shown, shaft (632) includes a longitudinally movable member (638) that configured to reside in a first longitudinal position (FIG. 10A), where movable member (638) blocks fluid from escaping from openings (636) and thus also lumen (634). However, movable member (638) is movable longitudinally to a position shown in FIG. 10B, where openings (636) are exposed and thus fluid may escape from lumen (634) out of openings (636). Other suitable configurations of shafts (532, 632), including openings (536, 636) to allow for cleaning of debris from lumens (534, 634), will be apparent to persons skilled in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a shaft assembly, comprising: (i) a shaft having a proximal end and a distal end, (ii) a lumen extending along at least a portion of the shaft, (iii) a lateral opening in the shaft, wherein the lateral opening is positioned between the proximal and distal ends, wherein the lateral opening is in fluid communication with the lumen, and (iii) a movable member configured to selectively cover the opening; and (b) an end effector at the distal end of the shaft.

EXAMPLE 2

The surgical instrument of Example 1, wherein the shaft assembly further comprises an acoustic waveguide, wherein the end effector comprises an ultrasonic blade in acoustic communication with the acoustic waveguide.

EXAMPLE 3

The surgical instrument of Example 2, wherein the shaft assembly further comprises an annular bumper surrounding the acoustic waveguide, wherein the movable member comprises the bumper.

EXAMPLE 4

The surgical instrument of Example 3, wherein the bumper is configured to attenuate vibrations of the acoustic waveguide.

EXAMPLE 5

The surgical instrument of any one or more of Examples 3 through 4, wherein the bumper is configured to effectively seal a proximal portion of the lumen from a distal portion of the lumen.

EXAMPLE 6

The surgical instrument of any one or more of Examples 3 through 5, wherein the bumper is movable from a first position to a second position, wherein the bumper is coincident with the opening in the first position, wherein the bumper is axially spaced from the opening in the second position.

EXAMPLE 7

The surgical instrument of Example 6, wherein the bumper is configured to substantially prevent fluid from exiting the lateral opening in the first position, wherein the bumper is configured to allow fluid to exit the lateral opening in the second position.

EXAMPLE 8

The surgical instrument of any one or more of Examples 6 through 7, wherein the acoustic waveguide is movable in concert with the bumper.

EXAMPLE 9

The surgical instrument of any one or more of Examples 1 through 8, wherein the movable member comprises a sleeve.

EXAMPLE 10

The surgical instrument of any one or more of Examples 1 through 9, wherein the movable member is movable from a first position where fluid is permitted to flow out of the lateral opening from the lumen, to a second position where fluid is substantially prevented from flowing out of the lateral opening from the lumen.

EXAMPLE 11

The surgical instrument of Example 10, wherein the movable member comprises an opening, wherein the opening of the movable member is configured to align with the lateral opening of the shaft in the first position, wherein the opening of the movable member is configured to not align with the lateral opening of the shaft in the second position.

EXAMPLE 12

The surgical instrument of any one or more of Examples 10 through 11, wherein the movable member is axially movable between the first and second positions.

EXAMPLE 13

The surgical instrument of any one or more of Examples 10 through 12, wherein the movable member is rotatable between the first and second positions.

EXAMPLE 14

The surgical instrument of any one or more of Examples 1 through 13, further comprising a fluid cleaning tray that includes at least one conduit, wherein the at least one conduit is configured to be fluidly coupled with the opening.

EXAMPLE 15

The surgical instrument of Example 14, further comprising a source of fluid.

EXAMPLE 16

A cleaning system, comprising a cleaning tray, the cleaning tray comprising: (i) a support portion, (ii) an inlet port, (iii) a main conduit in fluid communication with the inlet port, and (iv) at least one secondary conduit extending from the main conduit; wherein the secondary conduit is configured to be fluidly coupled to a shaft of a surgical instrument.

EXAMPLE 17

The cleaning system of Example 16, further comprising a surgical instrument, the surgical instrument comprising a shaft defining a lumen and including an opening, wherein the opening is configured to receive a portion of the at least one secondary conduit such that fluid may be directed into the inlet port, through the main conduit, into the at least one secondary conduit, and into the lumen of the shaft.

EXAMPLE 18

The cleaning system of Example 17, wherein the at least one secondary conduit comprises a connecting portion, wherein the connecting portion is configured to effectively seal the opening of the shaft when the connecting portion is received in the opening of the shaft.

EXAMPLE 19

The cleaning system of Example 18, wherein the connecting portion comprises a groove configured to receive a portion of a sidewall of the shaft.

EXAMPLE 20

A surgical instrument, comprising: (a) a shaft assembly, comprising: (i) a shaft having a proximal end and a distal end, (ii) a lumen extending along at least a portion of the shaft, (iii) an acoustic waveguide extending through the lumen, and (iv) a lateral opening in the shaft, wherein the lateral opening is positioned between the proximal and distal ends, wherein the lateral opening is in fluid communication with the lumen; and (b) an ultrasonic blade, wherein the ultrasonic blade is in acoustic communication with the acoustic waveguide.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) a shaft assembly, comprising:
        (i) a shaft having a proximal end and a distal end,
        (ii) a lumen extending along at least a portion of the shaft,
        (iii) a lateral opening in the shaft, wherein the lateral opening is positioned between the proximal and distal ends, wherein the lateral opening is in fluid communication with the lumen,
        (iv) a movable member configured to selectively cover the lateral opening, wherein the movable member extends around the entire circumference of a longitudinal portion of the shaft, and
        (v) an acoustic waveguide; and
    (b) an end effector at the distal end of the shaft, wherein the end effector comprises:
        (i) a pivoting clamp arm coupled with the shaft, and
        (ii) an ultrasonic blade in acoustic communication with the acoustic waveguide.

2. The surgical instrument of claim 1, wherein the movable member comprises a sleeve.

3. The surgical instrument of claim 1, wherein the movable member is movable from a first position where fluid is permitted to flow out of the lateral opening from the lumen, to a second position where fluid is substantially prevented from flowing out of the lateral opening from the lumen.

4. The surgical instrument of claim 3, wherein the movable member is axially movable between the first and second positions.

5. The surgical instrument of claim 1, further comprising a fluid cleaning tray that includes at least one conduit, wherein the at least one conduit is configured to be fluidly coupled with the lateral opening.

6. The surgical instrument of claim 5, further comprising a source of fluid.

7. The surgical instrument of claim 1, wherein the shaft assembly further comprises an inner tube coaxially disposed in the lumen of the shaft.

8. The surgical instrument of claim 7, wherein the inner tube has a proximal end, a distal end, and a lumen extending therebetween, wherein the inner tube includes a lateral opening positioned between the proximal and distal ends of the inner tube, wherein the lateral openings of the shaft and inner tube are longitudinally adjacent each other when the pivoting clamp arm is in an open position, such that the lateral openings are in fluid communication with the lumen of the inner tube.

9. The surgical instrument of claim 8, wherein the movable member is configured to selectively seal the lateral openings such that substantially no fluids enter or exit from the lateral openings through the lumen of the inner tube.

10. The surgical instrument of claim 1, wherein the shaft includes a proximal pin and a distal pin, wherein the proximal pin is configured to selectively prevent proximal movement of the movable member and the distal pin is configured to selectively prevent the distal advancement of the movable member past a certain distal position.

11. A surgical instrument, comprising:
(a) a shaft assembly, comprising:
  (i) an outer tube having a proximal end and a distal end, wherein the outer tube includes a lateral opening positioned between the proximal and distal ends of the outer tube,
  (ii) an inner tube coaxially disposed in the outer tube, wherein the inner tube has a proximal end and a distal end, wherein the inner tube includes a lateral opening positioned between the proximal and distal ends of the inner tube,
  (iii) a lumen extending along at least a portion of the inner tube, wherein the lateral openings of the inner and outer tubes are in fluid communication with the lumen,
  (iv) an acoustic waveguide extending through the lumen, and
  (iv) a movable member that is selectively movable from a first position where fluid is permitted to flow from the lumen out of the lateral openings of the inner and outer tubes, to a second position where fluid is substantially prevented from flowing from the lumen out of the lateral openings of the inner and outer tubes; and
(b) an ultrasonic blade, wherein the ultrasonic blade is in acoustic communication with the acoustic waveguide.

12. The surgical instrument of claim 11, further comprising a pivoting clamp arm coupled with the shaft assembly, wherein the lateral openings of the inner and outer tubes are longitudinally adjacent each other when the pivoting clamp arm and the ultrasonic blade are in an open position.

13. A surgical instrument, comprising:
(a) a shaft assembly, comprising:
  (i) a shaft having a proximal end and a distal end,
  (ii) a lumen extending along at least a portion of the shaft,
  (iii) a lateral opening in the shaft, wherein the lateral opening is positioned between the proximal and distal ends, wherein the lateral opening is in fluid communication with the lumen,
  (iv) a movable member configured to selectively cover the opening, wherein the movable member is movable relative to the shaft between at least first and second positions,
  (v) proximal and distal pins configured to selectively prevent axial movement of the movable member, wherein the movable member is located between the proximal and distal pins in the first position, wherein the movable member is located proximal to the proximal pin in the second position; and
(b) an end effector at the distal end of the shaft, wherein the end effector is operable to apply electrosurgical energy to tissue, apply ultrasonic energy to tissue, apply staples to tissue, apply sutures to tissue, or apply clips to tissue.

14. The surgical instrument of claim 13, wherein the proximal pin is resiliently biased radially outwardly from a longitudinal axis of the shaft assembly to allow proximal movement of the movable member.

15. The surgical instrument of claim 14, wherein the proximal pin is configured to move inwardly toward the longitudinal axis of the shaft assembly such that the proximal pin no longer impedes or prevents proximal movement of the movable member, wherein the proximal pin is configured to extend back outwardly once a distal end of the movable member is positioned proximally of the proximal pin.

16. The surgical instrument of claim 13, wherein the shaft assembly further comprises an inner tube coaxially disposed in the shaft, wherein the inner tube has a proximal end and a distal end, wherein the inner tube includes a lateral opening positioned between the proximal and distal ends of the inner tube, wherein the lateral openings of the shaft and inner tube are longitudinally adjacent each other when the end effector is in an open position.

17. The surgical instrument of claim 13, wherein the movable member is located entirely between the proximal and distal pins in the first position.

18. The surgical instrument of claim 13, wherein the shaft assembly further comprises an acoustic waveguide extending through the lumen, wherein the end effector further comprises an ultrasonic blade, wherein the ultrasonic blade is in acoustic communication with the acoustic waveguide.

19. The surgical instrument of claim 18, wherein the end effector further comprises a pivoting clamp arm coupled with the shaft.

20. The surgical instrument of claim 13, further comprising a fluid source containing fluid, wherein when the movable member is in the first position the fluid from the fluid source is configured to flow through the lumen and be prevented from exiting through the lateral opening by the movable member, wherein when the movable member is in the second position the fluid from the fluid source is configured to flow through the lumen and exit through the lateral opening.

* * * * *